US006103687A

United States Patent [19]
Cody et al.

[11] Patent Number: 6,103,687
[45] Date of Patent: Aug. 15, 2000

[54] NON-VOLATILE QUATERNARY AMMONIUM COMPOSITIONS AND THEIR USES

[75] Inventors: Charles Cody, Robbinsville; Araxi Chiavoni, Trenton, both of N.J.; Barbara Campbell, Bristol, Pa.; Edward Magauran, Westampton, N.J.

[73] Assignee: Elementis Specialties, Rheox Inc., Hightstown, N.J.

[21] Appl. No.: 09/064,723

[22] Filed: Apr. 23, 1998

Related U.S. Application Data

[63] Continuation-in-part of application No. 08/745,906, Nov. 7, 1996, abandoned, which is a continuation of application No. 08/385,295, Feb. 10, 1995, abandoned.

[51] Int. Cl.$^7$ .................. C11D 1/62; C11D 3/43
[52] U.S. Cl. .................. 510/504; 510/123; 510/136; 510/137; 510/158; 510/159; 510/174; 510/487; 510/488; 510/504; 510/515; 424/70.28; 514/846
[58] Field of Search .................. 510/123, 136, 510/137, 158, 159, 174, 487, 488, 504, 515; 424/70.28

[56] References Cited

U.S. PATENT DOCUMENTS

| 4,946,671 | 8/1990 | Bissett et al. | 424/59 |
| 4,976,953 | 12/1990 | Orr et al. | 424/47 |

*Primary Examiner*—Mark Kopec
*Assistant Examiner*—Gregory R. Delcotto
*Attorney, Agent, or Firm*—Michael J. Cronin

[57] ABSTRACT

Quaternary ammonium compositions are described which are made in diluents based on vegetable oil such as soya bean oil. Such diluents remain as diluents in the final product and generally have a vapor pressure of 1 mm of Hg or less at 25° C., and are liquid at ambient temperature. The liquid quaternary ammonium compound/diluent compositions have low toxicity and low volatile organic compound emission rates and high flash points, and can be tailored to particular applications. Such applications include use in fabric softeners, as cosmetics ingredients, deinking additives, surfactants, and reaction materials in the manufacture of organoclays.

3 Claims, 1 Drawing Sheet

NON-VOLATILE QUATERNARY AMMONIUM COMPOSITIONS AND THEIR USES

This is a continuation-in-part of U.S. patent application Ser. No. 08/745,906, filed Nov. 7, 1996, now abandoned which was a continuation of U.S. patent application Ser. No. 08/385,295 filed Feb. 10, 1995 now abandoned.

BACKGROUND OF THE INVENTION

1. Field of the Invention

Quaternary ammonium salts or "compounds" are tetra-substituted ammonium salts. They have a large number of commercial applications, including uses as ingredients for fabric softeners, as reaction materials in the manufacture of organophilic clays, as cosmetic ingredients, and as bactericidal agents. The chemical reaction processes used to synthesize quaternary ammonium compounds normally require the use of a non-reactive solvent to reduce the viscosity of the amines, particularly tertiary amines, prior to and during quaternization. The solvent most often employed commercially is isopropyl alcohol ("IPA"). Upon completion of the quaternization reaction process, the resulting quaternary ammonium compounds remain in solution, and are commonly sold as quaternary ammonium compositions in such a solvent mixture, or are dried, ground and then sold as relatively solvent-free powders.

In many applications using quaternary ammonium compounds the presence of solvents such as isopropyl alcohol diminishes the desired performance of the quaternary compound and adds environmental and manufacturing hazards due to the isopropyl alcohol's flammability, volatility and toxicity. Drying techniques have been developed which are capable of removing isopropyl alcohol from certain quaternary—solvent mixtures, but are not generally employed, because they add significant manufacturing costs, while failing to remove all of the isopropyl alcohol.

2. Summary of the Invention

The present invention involves the discovery that quaternary ammonium compositions, comprising quaternary ammonium compounds synthesized using specified diluents and the diluents in which the compounds were synthesized, provide improved properties and possess numerous advantages over essentially similar quaternary ammonium compounds quaternized using isopropyl alcohol or other prior art solvents.

Quaternary manufacturers employing the new invention, in addition to obtaining superior products, will also obtain the flexibility to utilize specific diluents selected either to promote beneficial effects in the ultimate product from the presence of the novel diluent, or at a minimum, to avoid existing deleterious effects on the systems of quaternary ammonium compound applications caused by IPA contamination.

Such use will also lead to improved product handling properties by significantly reducing the flammability, toxicity and environmental hazards associated with quaternary ammonium compounds made and sold with traditional volatile vehicles, and will open new markets to such products.

Particularly beneficial uses are in providing ways of making improved organoclays, cosmetic products including shampoos, and fabric softeners, as well as new uses of quaternary ammonium compounds as additives for the deinking of wastepaper pulp and as surfactants for laundry products.

3. Description of the Prior Art

Quaternary Ammonium Compounds

Quaternary ammonium compounds (sometimes abbreviated as "quats") of the type useful in this invention typically are salts of organic cations which have a positive charge localized on a single nitrogen atom and a charge neutralizing anion designated M⁻.

Quaternary ammonium compounds have the following formula:

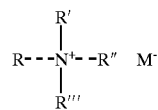

These quaternary ammonium compounds may be described as having four moieties where R is an organic radical and R', R" and R'", (the remaining groups attached to the central nitrogen atom), are typically selected from the group consisting of (a) alkyl groups; (b) aralkyl groups which are benzyl and substituted benzyl moieties; (c) aryl groups such as phenyl; (d) beta, gamma-unsaturated groups having six or fewer carbon atoms, (e) hydroxyalkyl groups having 2 to 6 carbon atoms; (f) ester groups and (g) hydrogen. The principal groups above are most often derived from naturally occurring fats or oils such as tallow, corn oil, soybean oil, cottonseed oil, castor oil, linseed oil, safflower oil, palm oil, peanut oil and the like. Mixtures of oils are commonly employed. The oil may be of natural sources, or a synthetic version of same, or modifications of a naturally occurring oil using known techniques. A broad listing of the useful components used to make quaternary ammonium compounds ("quats") is described in U.S. Pat. No. 5,336,647.

M⁻ is an anion which usually is chloride, methyl sulfate, bromide, iodide, hydroxyl, nitrite or acetate. The anion accompanying the organic cation is selected so as not to affect adversely the intended use of the quaternary ammonium compound, and may optionally be selected to impart unique characteristics to the quaternary compound.

In addition to the uses previously mentioned, these quaternary ammonium compounds also find utility as surfactants, anti-static agents, flotation agents, biocides, and, as stated, as reactants in the formation of organically-modified clay rheological control additives for paints, coatings, drilling muds and the like. In addition, polyquaternary compounds with more than one nitrogen atom have been utilized and are also included in the definition of quaternary ammonium compounds.

Processes of Making Quaternary Ammonium Compounds

The manufacture and preparation of quaternary ammonium compounds is achieved by techniques well-known in the art. When preparing a quaternary ammonium salt, one skilled in the art can prepare a dialkyl secondary amine, for example, by the hydrogenation of nitrites, and then form the methyl dialkyl tertiary amine by reductive alkylations using formaldehyde or dimethoxymethane as a source of the methyl radical. A commercial manufacturing process typically involves various stages, including those resulting in the creation of nitrites, primary amines, secondary and tertiary amines, and finally the quaternary compound itself.

The manufacturing process generally involves saturation of fatty acids derived from tallow, or of a commercial natural oil, by hydrogenation as an early step. This has led manufacturers to use the term, "hydrogenated tallow", or "HT", when describing common quaternary ammonium compounds, even those not exclusively derived from tallow fatty acids. Saturated, relatively long-chain hydrocarbon molecules are typically solids or very highly viscous liquids at room temperatures. They may be liquified by heating, but, particularly as the molecular weight of the intermediate products is increased in the course of the manufacturing process, the heat-induced liquification will not compensate for increasing viscosity, which win inhibit subsequent manufacturing steps. Accordingly, the quaternization step typically has been done in a liquid medium in order to solvate and reduce the viscosity of the both the starting material and the reaction products, and to reduce foaming. The medium used for commercial processing has almost universally been isopropyl alcohol (IPA).

Quaternization reactions are typically carried out in the presence of an inorganic alkali—such as sodium bicarbonate, sodium hydroxide, sodium or calcium carbonate—to react with any acid that may be formed as a by-product from the reaction of the alkylating agent (typically an alkyl or aralkyl halide) with labile hydrogen compounds contained within the reaction mixture. Such acidic materials form salts with the amine reactant, deactivating it toward quaternization. Such labile hydrogen compounds include, but are not limited to, primary and secondary amines—typically from incomplete reductive alkylation of the amine in the preceding step—water, and, when an alcoholic diluent is used as the reaction medium, the reaction solvent itself. Thus, while a chemical such as isopropanol will generally serve to accelerate the reaction of the alkylating agent with the amine and the reaction of any acidic by-products with the inorganic alkali, it win also reacts with the alkylating agent to generate unwanted acidic compounds and consumes the alkylating agent.

After manufacture, unless expensive vacuum distillation or freeze drying and grinding processes are later performed to produce a powdered product, the commercial quaternary ammonium compound is then generally sold in IPA solution, with typical activities ranging from 25 to 85 percent quaternary ammonium compound. Customers typically have no commercial use for the IPA either when blending the quat (or similar product) in the customer's process or product, such as fabric softener manufacture, or when using it as a reactant, for example in the manufacture of organoclays. Organoclays are the reaction product of smectite-type clay and quaternary compounds. See for example U.S. Pat. No. 4,105,578. The IPA often is discharged into a sewer leading either to a publicly owned water treatment facility or to a permitted direct discharge, or is volatilized and exhausted to the atmosphere when the organoclay is dried. As an alternative, significant expenses may be incurred for capture and reuse of the IPA from the effluent or pre-atmospheric emissions. As environmental controls on indirect dischargers, direct permitted dischargers, and emitters of volatile organic contaminants ("VOC's") are tightened, the cost of IPA disposal has been increasing at a rate several times that of inflation.

Several prior art references describe the various media, including IPA, which have been used to provide the volatile liquid solvent vehicle for quaternary ammonium compound manufacture. U.S. Pat. No. 2,775,617 describes a process for the preparation of defined quaternary ammonium compounds using animal fat tallow oils as starting ingredients. The patent describes the preparation of quaternary ammonium compounds and more particularly the preparation of tetra-alkylammonium compounds by the alkylation of alkyl secondary amines with alkyl halides. The patent teaches the use of the lower alcohols, particularly n-butanol, as solvent media for the reaction. U.S. Pat. No. 2,644,003 describes the making of quaternary ammonium compounds having very strong bactericidal activity using, as the reaction solvents, benzene, toluene, xylene, acetone, ethyl and butyl acetate. The compounds are useful for the disinfection of human skin, as well as the disinfection of utensils including medical instruments. U.S. Pat. Nos. 2,950,318 and 3,175,008 relate to improved processes for the production of quaternary ammonium compounds employing, as the solvent vehicle, one of the low-boiling alcohols including methanol, ethanol, propanol, isopropanol, butanol, isobutanol, and the like, with the preferred solvent being isopropyl alcohol, together with a minimum amount of water. Upon completion of the reaction, the mixture produced contains the quaternary compound in an aqueous alcoholic solution. While not commercially significant certain quaternary manufacturers have made their products in glycols as the solvent including propylene glycol, hexylene glycol and diethylene glycol.

Relatively recent U.S. Pat. No. 4,857,310 shows the preparation of quaternary ammonium compounds from cosmetic and toiletry compositions from castor oil triglycerides carried out using, in one stage, solvents such as toluene, chloroform and dichloromethane, and in a second stage, the organic vehicle ethanol introduced at an elevated temperature. The resulting product is then dried under vacuum at 80° C. to remove the ethanol.

The media described in the prior art, in the main, involve mostly volatile organic compositions which share a number of properties, the most important of which is the low temperature at which they exhibit a vapor pressure of approximately 1mm. For example ethanol exhibits a vapor pressure of 1mm, at a temperature of $-31°$ C. while toluene's temperature is $-26.7°$ C. and methanol's is $-44°$ C. While glycols have vapor pressures of 1 mm or more at higher temperatures, they present problems of toxicity, odor, flammability and solubility in water systems where the quaternary may be used, and thus they have not been widely employed. Most of the solvents employed in the conventional manufacture of quaternary ammonium compounds can be further characterized as having toxicity, low viscosity, low flash and freezing points. In particular, the vapor pressure of almost all the prior art vehicles substantially exceeds 1 mm of Hg at 25° C.

U.S. Pat. No. 4,096,072 shows a fabric conditioning particle containing two essential components and other minor amounts of other fabric treating agents including perfumes and anti-bacterial agents. One of the essential components is a quaternary ammonium salt fabric conditioning compound and the second is hydrogenated castor oil. This patent describes hydrogenated castor oil as "hardened" and chemically converted by reacting castor oil with hydrogen. The quaternary salt component is described as "co-melted" with the hydrogenated castor oil and then converting the molten mass into solid particles, i.e. cooling to a solid mass followed by grinding.

European Patent No. 444,229 shows the manufacture in a single step reaction of a four component composition which composition includes a quaternary ammonium compound, fatty acid, tertiary amine, and methyl ester. The reaction uses fatty acid as a reactant, likely in an excess amount, so that some fatty acid remains unreacted. The composition described is in solid form and can be flaked or powdered.

U.S. Pat. No. 4,795,573 describes a mixture of two different salts, one of them, salt (A) being a standard quaternary compound with salt (B) a branched compound. The patent describes the product in a 75% solution with the isopropyl alcohol (IPA) in which it was made.

Quaternary ammonium compounds are usually prepared in complex and expensive stainless-steel or glass-lined equipment. The amine, with or without water, is loaded into the reactor and heated to the proper temperature (usually 80–100° C.), and an alkylating reagent is added. Quaternization of tertiary amines with alkyl halides is bimolecular. The rate of reaction is influenced by a number of factors, including the nature and quality of the starting materials, the basicity and nucleophilicity of the amine, stearic effects, temperature, reactivity of the halide, and the polarity and other characteristics of the solvent used. Such solvents, in addition to providing liquidity, also assist the reaction by stabilizing the ionic nature of the transition stage of the quaternization reaction.

Uses of Quaternary Ammonium Compounds

The use of quaternary ammonium compounds to make organophilic clays is described in a large number of patents. Illustrative patents which describe such organophilic clays and their use as thickeners and rheological additives include U.S. Pat. Nos. 4,894,182, 4,450,095 and 4,434,075. Organoclays are the reaction products of smectite clays, including hectorite and bentonite, with one or more quaternary ammonium compounds.

Volume 19 of the *Encyclopedia of Chemical Technology* at pages 529 to 530 describes the various uses of quaternary ammonium compounds as fabric softeners. There are three types of commercial products disclosed: the first is a 4–8 wt % dispersion of quaternary ammonium compound, which is added to the rinse cycle of the washing process by the washing machine user. The second commercial product is a quaternary ammonium compound formulation applied to a nonwoven sheet or a polyurethane foam, which is added with the wet clothes into the dryer by the homemaker. This product formulation contains a transfer agent, usually a fatty-acid ester, which allows the quaternary ammonium compound to transfer from the substrate to the wet clothes. The third type of product is a combined detergent, softener and antistatic formulation containing quaternary ammonium compounds, which allows the introduction of all necessary ingredients into the wash cycle of the washing process. In all cases, the benefits to the user are fabric softening, antistatic properties, ease of ironing, and odor improvement, the latter because of the common addition of perfumes to the formulation. The most widely used, and most effective, quaternary ammonium compounds used for fabric softening purposes are the dimethyl bis[hydrogenated tallow] ammonium chlorides and methyl sulfates ("2M2HT").

Another significant use for quaternary ammonium compounds is in certain cosmetics, particularly for hair treatment. Quaternaries have a high affinity for proteinaceous substrates, and this property makes them useful for hair treatment. They impart antistatic effects, increase hair wetting, improve wet and dry combing, and improve feel and luster. Other cosmetic uses are widely diversified, and the quaternary ammonium compound formulations vary from one cosmetic manufacturer to another, depending on the qualities to be emphasized. In some cases, the solvent with the quaternary ammonium compound is acceptable, while in others it must be removed, for example, by spray drying.

Another important use of quaternary ammonium compounds is in compositions for deinking wastepaper, which is a growing industry both in the United States and throughout Europe. Applicant's assignee in pending U.S. Pat. No. 5,336,372 describes a process for deinking wastepaper in an aqueous flotation process utilizing organoclays formed in situ in the deinking apparatus by the use of quaternary ammonium compounds as deinking chemicals, particularly 2M2HT. U.S. Pat. No. 4,935,096 discloses a method for deinking waste printed paper by using quaternized alkyl tallow compounds as deinking surfactants in a washing process. Since quaternary compounds in commercial use contain IPA, or other similar soluble solvents such as hexylene glycol, the constantly recycled water used in commercial deinking can be adversely impacted by present-day compositions, since the increasing concentrations of such solvents result in process difficulties, solvent build-up and disposal problems, and eventually lead to discharge into the environment.

Figure 1:
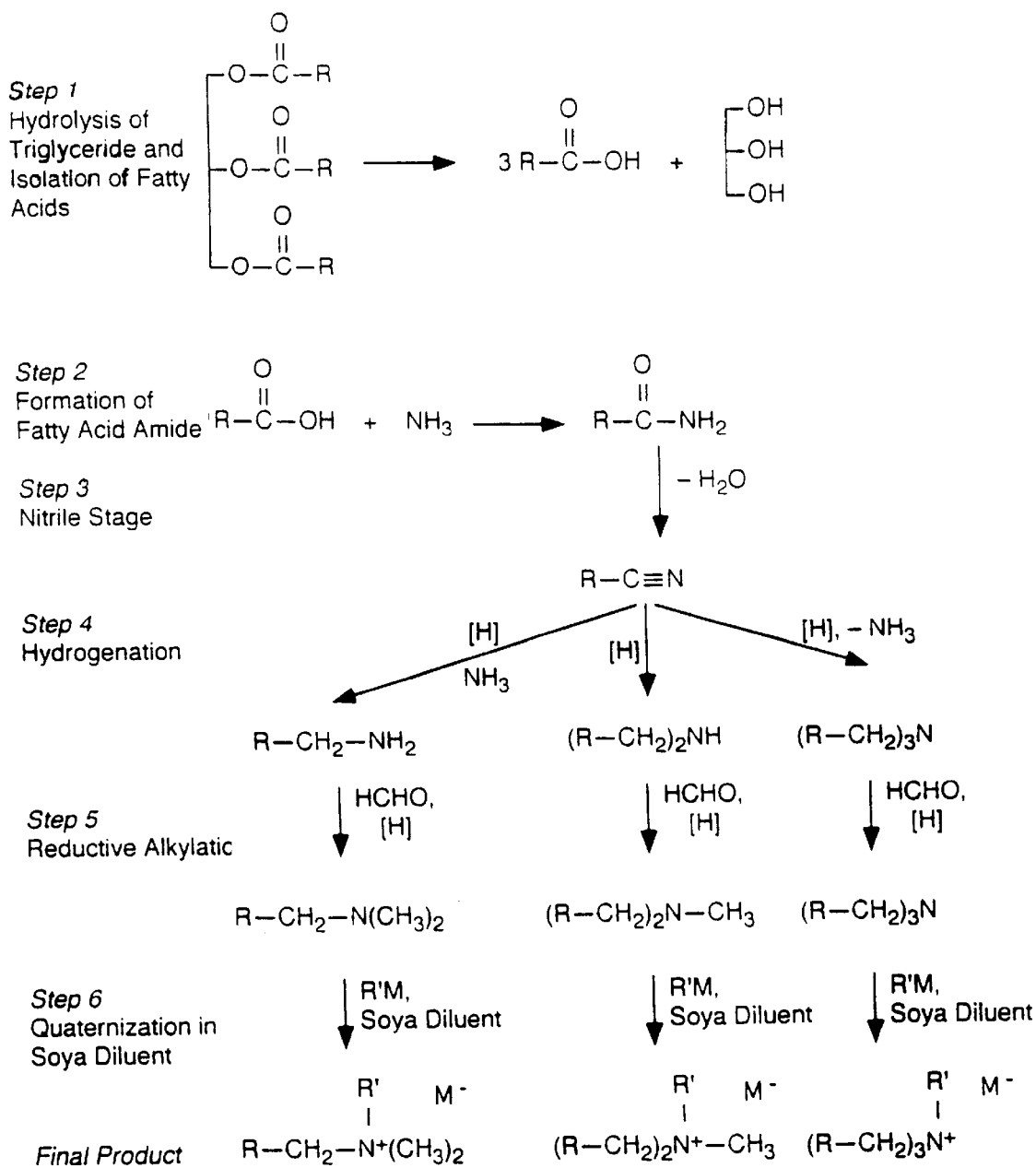
FIG. 1 is a block diagram illustration of a commercial process for manufacturing quaternary ammonium compound of a preferred type useful in the invention, most particularly 3MHT. In Step 1, the starting material, a fatty acid triglyceride, is saponified and the fatty acids isolated. The fatty acids is reacted with ammonia to form an amide in Step 2. Saturation of the fatty alkyl radicals, if required, may be accomplished by catalytic hydrogenation of either the fatty tridyercerides prior to saponification or of the resulting fatty acids. The nitrile in Step 3 is converted by catalytic hydrogenation. Depending on the reaction conditions employed, the principal product of this catalytic hydrogenation is either a primary, secondary or tertiary amine. For instance, if the hydrogenation is carried out in the presence of high ammonia pressure, the principal product is a primary amine; alternatively, if the hydrogenation is carried out in the absence of added ammonia partial pressure, the principal product is a secondary amine. Usually the amine product is then subjected to reduction alkylation using formaldehyde or a formaldehyde equivalent in Step 5 to form a tertiary amine; the product of this reductive alkylation of a primary amine is a dimethyl alkyl amine and, of a secondary amine, a methyl dialkyl amine. Although tertiary amines will not undergo reduction alkylation, the products of the catalytic hydrogenation of nitriles to form them are usually subjected to reductive alkylation conditions to convert any primary and secondary amine impurities to tertiary amines prior to subjecting to quaternization conditions.

These tertiary amines are then diluted with a non-volatile soya diluent prior to Step 6 after the alkylating or quaternizing agent has been added in Step 5, followed by Step 6, the quaternization step. As shown in the diagram, a medium (in this case, soya oil) is incorporated before the start of Step 6 to give liquidity and proper viscosity to the reaction. The final commercially-made quaternary ammonium compound typically consists of approximately 94% pure 3MHT, shown on the left of the line of designated Final Product, together with a mixture of other "impurity" ingredients, primarily two other quaternaries. The total composition is in mixture in an approximate ratio of 9 parts quaternary ammonium compound to 1 part soya diluent, although other ratios are also possible.

Other quats can be manufactured by the process described, or by other known processes, using other diluents of the inventive type provided they have vapor pressure of about 1 mm or less at 25° C.

DESCRIPTION OF THE PREFERRED EMBODIMENTS

The invention is the discovery that certain diluents, when used in the manufacture of quaternary ammonium compounds, unexpectedly produce compositions which provide improved performance in various end uses, both traditional uses such as the manufacture of organoclays and detergent surfactants, and potential new uses in soap and cosmetic manufacture and as deinking chemicals for wastepaper treatment.

Diluents are inert liquid substances added to other substances so that the volume of the latter substance is increased and its concentration per unit volume descreased—they also make the substance "thinner" or more liquid than before their addition. The term inert, as used herein, means that the diluent is not chemically altered during the various manufacturing steps employed to make the quaternary compound.

Diluents used in the processing to create the novel quaternary ammonium compositions are liquid vegetable oils including soya bean oil, castor oil, safflower oil and coconut oil, where the term vegetable means obtained from plants or plant material. Such diluents generally have a vapor pressure of 1 mm of Hg or less at 25° C. and are liquid at ambient temperature or melt and become fluids below the quaternization reaction temperature encountered. Particularly preferred process diluents to prepare quaternary ammonium compositions according to the present invention include soya bean oil and safflower oil.

The resultant quaternary ammonium composition made using the above diluents in the manufacturing process, have the beneficial qualities of low volatile organic compound emission rates, high flash points, are in liquid form at room temperatures, and are generally not toxic. The products of this invention comprise a mixture of a quaternary ammonium compound and the vegetable oil diluent used, which we call a quaternary/diluent composition.

Another approach to forming similar quaternary/diluent composition, while not preferred, is to form the quaternary ammonium compound in a conventional prior art solvent, remove the solvent by drying or evaporation, then physically combine the dried quaternary compound with the preferred new diluent in a blender, or other apparatus, heating the quaternary compound to melt it as required, and then mixing with the resultant product with the diluents of the invention. The fact that the quaternary compound was originally made in the conventional solvent, normally IPA, provides an inferior product because there remains residual IPA in the composition.

The manufacturing process, using diluents of the present invention, of four specific quats having wide and varied commercial uses is particularly preferred; dimethyl bis [hydrogenated tallow] ammonium chloride ("2M2HT"), benzyl dimethyl hydrogenated tallow ammonium chloride ("B2MHT"), trimethyl hydrogenated tallow ammonium chloride ("3MHT") and methyl benzyl bis[hydrogenated tallow] ammonium chloride ("MB2HT").

It should be observed that the diluent used need not be restricted to single species or moieties having uniform chain lengths or structures. In fact, combinations or mixtures of different acceptable diluents can lead to satisfactory products, such as a mixture of 50% soya oil and 50% safflower oil. In addition, for example, a soya oil used may meet commercial specifications for virgin soya oil, while still containing other animal or vegetable oils, having soya oil of non-standard carbon chain length distribution, or containing carbon groups of chain lengths and in relative percentages typical of soya oil, but which were in fact derived from fatty oils or substances other than soya oil. Further, mixtures of the inventive diluents with prior art solvents can be used if the vapor pressure of the mixture is less than about 1 mm of Hg at 25° C.

Defoaming agents may be employed during synthesis of the inventive compositions. Typical defoaming agents include various alcohols, hydrocarbons, dimethyl polysiloxane, silicone-containing compounds, alcohol alkoxylates, propoxylated alkyl amines, polyacrylates, alkyleneoxide copolymers, fatty acids, fatty acid sulfonates and blends of fatty acids and esters in hydrocarbons. Preferred defoaming agents for use in synthesizing compositions of the present invention include dimethyl polysiloxanes and silicone-containing compounds. Particularly useful defoaming agents are those composed of dimethyl polysiloxane and silica, such as Dow Corning 1400 and 1410 antifoam agents.

Quaternary ammonium compositions prepared using the above diluents can generally be employed in the same applications as those prepared using isopropyl alcohol or similar prior art solvents. Common applications would include those as an ingredient in fabric softeners, hair conditioning agents, dispersants, flocculating agents, germicides, algicides, surfactants, phase transfer catalysts, emulsifiers, antistatic agents, and as reactants for the preparation of organically-modified clays. Importantly, new uses not presently served satisfactorily by quaternary ammonium compounds, such as improved fabric softeners, deinking and cosmetics targeted to feminine consumers, can now be served. Preparation of the quaternary ammonium compound in the new diluents also eliminates the additional processing steps (vacuum or spray drying and grinding) which may be required to remove and dispose of most of the isopropyl alcohol or similar prior art solvents in certain fabric softener manufacturing processes.

Another beneficial economic aspect of the invention is cost reduction. In the making of a quaternary ammonium-modified organoclay, for example, quaternary ammonium compounds such as 2M2HT are brought into a manufacturing plant as a mixture of 83% quat/17% IPA and water, then reacted, commonly with an aqueous slurry of smectite clay, to form a smectite organoclay complex, with most of the unwanted and unneeded IPA dissolving in the waste water, with some adhering to the organoclay filter cake. Simple substitution of the compounds of this invention at the manufacturing stage will eliminate the IPA, with additional benefits resulting, since there is no IPA causing a disposal problem, nor will IPA be released to the atmosphere during organoclay filter cake drying or grinding. Furthermore, since the diluent is carried along with the organoclay, if a non-water soluble diluent is selected, the product yield per unit weight of quaternary reactant will be higher, also resulting in greater economy of usage versus the quaternary ammonium/prior art solvent situation. In addition, the diluent may be selected to provide synergistic effects to the organoclay during its usage, including effects such as improved wettability, enhanced dispersibility and reduction in moisture pick up. Synergistic effects are also possible in non-organoclay uses of the quaternary/diluent compositions of this invention, particularly in oil well drilling fluids.

The quaternary/diluent compositions of this invention can be used with wastepaper pulp aqueous systems as deinking additives. For example, a deinking organoclay may be formed in the aqueous system by adding the quaternary/diluent composition and one or more cation-exchangeable clays to the aqueous system, where these materials react to form the organoclay deinking agent. Alternatively, if the wastepaper to be treated contains cation-exchangeable clays, an organoclay deinking agent may be formed in the system without external clay addition by pulping the wastepaper to release the clay from the wastepaper and mixing in the quaternary/diluent composition to form the organoclay in situ. Conventionally formed quaternaries are difficult to use for deinking, because of the ultimate release of the IPA solvent to the water-ways.

Another deinking technique employing the new invention involves adding a blend, composed of one or more cation exchangeable clays mixed with the quaternary/diluent composition, to the aqueous system. Upon addition of the blend to the aqueous system, the clay reacts with the quaternary to form an organoclay deinking agent. In addition the quaternary may also react with any clay contained in the wastepaper. Another technique involves adding the quaternary/diluent composition to the ink, paper sizing, or paper itself before the paper is printed, pulping the wastepaper to liberate the quaternary/diluent composition, and then separately adding a clay, to the deinking tank, so that the clay and ammonium salt(s) react to form the deinking organoclay.

Deinking processes using the present invention successfully remove water-based (flexographic) and oil-based inks as well as chemicals in adhesive-backed labels and the like ("sticky components") from wastepaper. The particular ability to collect and float flexographic ink and remove sticky components, without IPA concerns, is a notable advantage of the invention over conventional deinking techniques using prior art commercial products.

Quaternary ammonium/diluent compositions of the present invention can also be used as surfactants. Such surfactants can find use in soaps, particularly specialty soaps and liquid soaps, cosmetics and hair treatments, as well as in performing surfactant functions in wastepaper deinking processes. Dishwashing liquids and shampoos can particularly benefit from the quaternary/diluent compositions of the instant invention, especially if diluents compatible with the product media involved are selected.

Organoclays using the novel quaternary/diluent compositions of this invention may be prepared by admixing the clay, the quaternary/diluent composition and water together, preferably at temperatures from about 20° C. to 100° C., and most preferably from 35° C. to 80° C., for a period of time sufficient for the quaternary compound to react with the clay. The reaction is followed by filtering, washing, drying and grinding. The quaternary/diluent composition may be added simultaneously with process reactants, or at separate intervals. The amount of such composition added to the clay must be sufficient to impart to the clay gelling and dispersion characteristics. The amount of quaternary compounds may be equal to or in excess of the milliequivalent ratio, which is the number of milliequivalents (m.e.) of the quaternary in the organoclay per 100 grams of natural clay, 100% active clay basis. A mixture of quaternary ammonium compounds either in the same or different diluents can also be utilized.

Organophilic clay gellants using quaternary/diluent compositions according to this invention are useful as rheological additives in both non-aqueous and aqueous systems such as inks, paints, varnishes, enamels, waxes, paint-varnishes, oil base drilling fluids, lubricants and greases, polyesters, epoxy resins, adhesives, sealants, cosmetics, detergents, and the like. Such organoclays can also be used directly as deinking additives or as soil remediation chemicals. For the above uses and others, the diluent is carried along in the system, and does not contribute to the release of volatile organic compounds (VOC) to the atmosphere.

Organoclays made with soya diluent, for example, when used to thicken soya-based systems such as certain modern printing inks are highly dispersible and compatible with such inks. The soya diluent remains on the organoclay during its manufacture—as soya oil has little significant solubility in water at temperatures below 100° C. at atmospheric pressure. Such a product is at least as effective as prior art organoclays made with quaternary compounds dissolved in conventional solvents, and eliminates the IPA disposal problem.

Another use for the inventive organoclay/diluent use is in drilling muds. Presently manufacturers of pure or blended low-aromatic mineral oil-based drilling muds separately add organoclays to the drilling mud composites. A further organoclay use is as an agricultural carrier to facilitate the delivery of various herbicides in an enhanced manner.

Quaternary ammonium/diluent compositions of the present invention can also be used as surfactants. Such surfactants can find use in soaps, particularly specialty soaps and liquid soaps, cosmetics and hair treatments, as well as in performing surfactant functions in wastepaper deinking processes. Dishwashing liquids and shampoos can particularly benefit from the quaternary/diluent compositions of the instant invention, especially if diluents compatible with the product media involved are selected.

Quaternary/diluent compositions of the present invention are particularly useful as fabric softeners, and can be simply and efficiently added, for example, to the rinse cycle in common washing machines used at home or in "laundromats". Since there is no IPA or traditional diluent in the quaternary/diluent composition, no spray drying or evaporation steps need be employed in the manufacturing process to make detergent or softener formulations, either liquid or solid, containing these inventive compositions. Odor in particular is improved, and a wide variety of fragrances and perfumes can be utilized in combination with the novel quaternary/diluent compound. The quaternary/diluent composition can be added to polyurethane foams or to anti-static/fabric softener sheets already in common use. The diluent utilized can be selected to facilitate dispersion in the aqueous washing medium, improve the water solubility of the quaternary ammonium compound and substitute for additives (or reduce the amount used) separately added to fabric softeners, such as coconut oil or surfactants. A particularly useful quaternary composition using the instant invention for fabric softeners is 2M2HT, in light of its high anti-static behavior and ready availability.

The selection of a proper diluent in the quaternary/diluent composition can eliminate or significantly reduce many of the negative consequences of contamination by the traditional quaternary solvent. Volatile solvents can alter the degree and consistency of form, dramatically reduce viscosity, change the wettability and solubility of additives, as well as contribute to the total volatile organic content. Solvents such as diethylene glycol can present toxicity and odor problem. As a direct result of their chemical compositions, such prior art solvents can also cause film porosity, blistering and wrinkling in coatings and films. These solvents can cause surface deposits which can result in a reduction of gloss and increased haze, alteration in adhesion and non-homogenous distribution of the quaternary compound.

The following examples are given to illustrate the invention, but are not deemed to be limiting thereof.

EXAMPLE 1

Flotation deinking tests were conducted on a quaternary ammonium composition consisting of 50% 2M2HT which had been diluented with soybean oil. The soybean oil replaced isopropyl alcohol eliminating the need to remove isopropyl alcohol using an expensive drying step. An in situ generated organoclay was formed in the wastepaper.

The 2M2HT/soybean oil sample was evaluated as a flotation deinking additive to a slurry of wastepaper composed of 35/35/30 water news/oil news/magazine. Wastepaper was pulped at 4% consistency with addition of 0.16% DTPA (diethylene triamine pentaacetic acid), 1% sodium silicate, 1% sodium hydroxide, 1% hydrogen peroxide, 0.0076% Brij 700 surfactant and the deinking additive. After pulping the stock was diluted to 1% consistency and flotation deinked. Water hardness was adjusted to 200 ppm using calcium chloride. For comparison, a sample of 86.36% 2M2HT synthesized in isopropyl alcohol was also evaluated. Data presented in Table I indicate that when compared at equal 2M2HT content, the 2M2HT/soybean oil composition provided deinked pulp brightness equal to that of the 2M2HT/IPA control.

TABLE I

|  | Hunter Lab Brightness (Top/Bottom) | | |
|---|---|---|---|
| Deinking Additive | 0 Min | 6 Min | 12 min |
| 1% 50% 2M2HT/Soybean Oil | 44.7/45.3 | 58.0/58.4 | 62.4/62.8 |
| 0.579% 86.36% 2M2HT/IPA | 42.7/44.8 | 59.0/59.5 | 62.7/62.9 |

EXAMPLE 2

Organoclays prepared by reacting a quaternary ammonium/soya oil composition with bentonite clay were prepared and evaluated in solvent-based paint. The bentonite clay was dispersed in water (3% solids) at 65° C. and then reacted, for 30 minutes with various amounts of 80/20 2M2HT/soya oil composition, filtered and dried at 105° C., before being milled in an impact mill (centrifugal) using a 0.5 mm screen. For comparison, an organoclay composed of bentonite clay reacted with conventional quaternary ammonium/IPA was also prepared. The resulting organoclays can be described as

| No. | Organoclay Composition | Quat m.e. | Theoretical % o.c.* | % S.B.O.** |
|---|---|---|---|---|
| 1 | 2M2HT/S.B.O./Bentonite | 118.3 | 90.6 | 9.4 |
| 2 | 2M2HT/S.B.O./Bentonite | 99.4 | 91.5 | 8.5 |
| 3 | 2M2HT/S.B.O./Bentonite | 90.9 | 91.9 | 8.1 |
| 4 | 2M2HT/IPA/Bentonite | 99.4 | 100 | 0 |

* Percent organoclay by weight
**Percent soya bean oil

The organoclay compositions described above were evaluated as rheological additives aliphatic gloss alkyd enamel paint formulation and compared to a conventional organoclay, Bentone 34, made with a quaternary compound in IPA. The organoclays were evaluated at a loading of 7.2 pounds of active organoclay per 100 gallons of paint. Paint formulations were prepared according to the procedure detailed in Addendum 1.

Data presented in Table II indicate that organoclay compositions prepared using the 80/20 2M2HT/soybean oil composition provided rheological performance similar to that provided by standard organoclays made with IPA containing quaternaries.

ADDENDUM I

ALIPHATIC GLOSS ALKYD ENAMEL - AIR DRY
0.7% RHEOLOGICAL ADDITIVE

| RAW MATERIAL | POUNDS | GALLONS |
|---|---|---|
| Beckosol 10-060 Alkyd Resin Solution | 105.76 | 13.25 |
| Mineral Spirits 66/3 | 70.60 | 10.91 |
| Organoclay Rheological Additive - Active | 7.17 | 0.51 |
| Mix 3 mins. @ 3000 RPM THEN: | | |
| Methanol/Water 95/5 @ 33% Polar Activator | 2.39 | 0.36 |
| Mix 5 mins. @ 3000 RPM THEN: | | |
| KRONOS® 2101 TiO$_2$ | 325.00 | 9.76 |
| Disperse 15 mins. @ 5000 RPM | | |
| Then letdown with: | | |
| Beckosol 10-060 (Alkyd resin solution) | 445.90 | 55.88 |
| ZR 6% NUXTRA Drier | 10.30 | 1.43 |
| CO 6% NUXTRA Drier | 3.42 | 0.46 |
| Exkin #2 Anti-skinning Agent | 2.00 | 0.25 |
| Mineral Spirits 66/3 | 54.70 | 8.45 |
| Mix 10 mins. @ low speed | | |
| | 1027.24 | 101.26 |

FORMULA WT/GAL: 10.15
PVC, %: 18.51
N.V. % (VOL): 52.95
N.V. % VEH (VOL): 43.15

TABLE II

TEST Type: ALKYD GLOSS ENAMEL

|  |  |  | ORGANOCLAY NUMBER | | | |
|---|---|---|---|---|---|---|
|  | Blank |  | 1 | 2 | 3 | 4 |
| Rheological Additive | None | Bentone 34 | As described | | | |
| Theoretical: | | | | | | |
| SBO, % | — | — | 9.4 | 8.5 | 8.1 | 0 |
| Organoclay % | 0 | — | 90.6 | 91.5 | 91.9 | 100 |
| Quat. M.E. % | — | — | 118.3 | 99.4 | 90.9 | 99.4 |
| Loading Level: Pounds per/hundred gallons | 0 | 7.20 | 7.86 | 7.86 | 7.86 | 7.20 |
| Polar Act Vator (P.A.): | — | — | YES | | | |
| Type P.A.: | — | — | MeOH/H$_2$O | | | |

TABLE II-continued

TEST Type: ALKYD GLOSS ENAMEL

| | | Blank | ORGANOCLAY NUMBER | | | |
| --- | --- | --- | --- | --- | --- | --- |
| | | | 1 | 2 | 3 | 4 |
| Paint, F.O.G. Final | | 6.5A | 6.5A | 6.5A | 6.5A | 6.5A | 6.5A |
| Stormer Visc. KU @ 77° F. | | 90 | 97 | 95 | 97 | 97 | 99 |
| Brookfield Visc., cps | | | | | | | |
| Spindle #5 | 10 RPM | 1100 | 2400 | 2200 | 2400 | 2500 | 2500 |
| Temp, 77° F. | 100 RPM | 1100 | 1610 | 1500 | 1590 | 1670 | 1710 |
| | T.I. | 1.00 | 1.49 | 1.47 | 1.51 | 1.50 | 1.46 |
| Leneta Sag, Mils | | 3.5 | 5.8 | 5.8 | 5.9 | 5.9 | 6.0 |
| Gloss, | | | | | | | |
| 60° | | 85 | 84 | 86 | 85 | 84 | 84 |
| 20° | | 76 | 73 | 76 | 72 | 73 | |

What is claimed:

1. A liquid quaternary ammonium composition consisting essentially of:

(a) a quaternary ammonium compound selected from the group consisting of dimethyl bis(hydrogenated tallow) ammonium chloride, benzyl dimethyl hydrogenated tallow ammonium chloride, trimethyl hydrogenated tallow ammonium chloride and methyl benzyl bis (hydrogenated tallow) ammonium chloride in an amount from about 50 to about 80% of the composition.

2. The composition of claim 1 wherein the liquid vegetable oil diluent is soya bean oil.

3. The composition of claim 2 wherein the liquid vegetable oil diluent was prepared from carbon groups derived from fatty oils or substances other then soya bean oil.

* * * * *

UNITED STATES PATENT AND TRADEMARK OFFICE
CERTIFICATE OF CORRECTION

PATENT NO.   : 6,103,687
DATED        : August 15, 2000
INVENTOR(S)  : Charles Cody, Araxi Chiavoni, Barbara Campbell and Edward Magauran It is certified that error appears in the above-identified patent and that said Letters Patent is hereby corrected as shown below:

Claims:

1. A liquid quaternary ammonium composition consisting essentially of:
 (a) a quaternary ammonium compound selected from the group consisting of dimethyl bis (hydrogenated tallow) ammonium chloride, benzyl dimethyl hydrogenated tallow ammonium chloride and methyl benzyl bis (hydrogenated tallow) ammonium chloride in an amount from about 50 to about 80% of the composition;
 (b) and a liquid vegetable oil diluent, where the diluent is in an amount from about 20 to about 50% of the composition, and
 wherein the quaternary ammonium compound component of the quaternary ammonium composition was synthesized using the diluent as a medium.

Signed and Sealed this

Eleventh Day of September, 2001

Attest:

*Nicholas P. Godici*

NICHOLAS P. GODICI
*Attesting Officer*   *Acting Director of the United States Patent and Trademark Office*